(12) United States Patent
Ploeg et al.

(10) Patent No.: US 8,754,288 B2
(45) Date of Patent: Jun. 17, 2014

(54) METHOD FOR THE PRODUCTION OF PINK COLORED CABBAGE

(75) Inventors: Sjaakvander Ploeg, Enkhuizen (NL); Wolfgang Ott, Kleve (DE); Renate Wunsche, Enkhuizen (NL); Erik Keurentjes, Enkhuizen (NL)

(73) Assignee: Syngenta Participations AG, Basel (CH)

( * ) Notice: Subject to any disclaimer, the term of this patent is extended or adjusted under 35 U.S.C. 154(b) by 701 days.

(21) Appl. No.: 12/739,512

(22) PCT Filed: Nov. 10, 2008

(86) PCT No.: PCT/EP2008/009458
§ 371 (c)(1),
(2), (4) Date: Sep. 10, 2010

(87) PCT Pub. No.: WO2009/062645
PCT Pub. Date: May 22, 2009

(65) Prior Publication Data
US 2011/0003033 A1  Jan. 6, 2011

(30) Foreign Application Priority Data
Nov. 16, 2007  (EP) ..................................... 07022265

(51) Int. Cl.
*A01H 1/02*   (2006.01)

(52) U.S. Cl.
USPC ........................................... 800/260; 800/306

(58) Field of Classification Search
None
See application file for complete search history.

(56) References Cited

U.S. PATENT DOCUMENTS 2,345,814 A    4/1944   Harrison

FOREIGN PATENT DOCUMENTS

WO    WO 96/21010    7/1996

OTHER PUBLICATIONS

Whipker et al (North Carolina Cooperative Extension Service, Horticulture Information Leaflet 507, 1998).*
Dickson et al (Cabbage Breeding, Chapter 11, In Breeding Vegetable Crops, pp. 395-432, 1986).*
J.R. Baggett and D. Kean, Euphytica, 1984, 33, pp. 587-890.

* cited by examiner

*Primary Examiner* — Shubo (Joe) Zhou
*Assistant Examiner* — Keith Robinson
(74) *Attorney, Agent, or Firm* — Karen Magri (57) ABSTRACT

The invention relates to pink *Brassica oleracea capitata* (cabbage) plants and a production method thereof. The invention relates furthermore to the use of pink cabbage for the production of pink pickled cabbage and pink salad.

6 Claims, 2 Drawing Sheets

Figure 1: Spectrum of the anthocyanins present in white, pink and red cabbage leaves Figure 2: staining properties of cell sap of red cabbage compared to pink and white cabbage.

METHOD FOR THE PRODUCTION OF PINK COLORED CABBAGE

CROSS-REFERENCE TO RELATED APPLICATIONS

This application is a national phase application of International Application No. PCT/EP2008/009458, filed Nov. 10, 2008, which claims priority to European Application No. 07022265.8, filed Nov. 16, 2007.

FIELD OF THE INVENTION

The invention relates to pink *Brassica oleracea capitata* (cabbage) plants and a production method thereof. The invention relates furthermore to the use of pink cabbage for the production of pink pickled cabbage and pink salad.

The cabbage (*Brassica oleracea capitata*) is a leaf vegetable and the so-called 'cabbage head' is widely consumed raw, cooked, or preserved in a great variety of dishes. More than 400 *Brassica oleracea capitata* cultivars with different leave colours (mainly white and red) are available and widely used for food production. Cabbage plants are used for the preparation of salad and for the production of pickled cabbage (also called sour cabbage or Sauerkraut). Sauerkraut is finely sliced cabbage fermented by various lactic acid bacteria. Roughly 50% of the German annual production of white cabbage is used to produce pickled cabbage.

Red cabbage contains large amount of the so called anthocyanins, which are a type of flavanoid pigments and are responsible for the colouration of red cabbage leaves. These pigments are water soluble and are dissolved in the vacuole of the plant cells. Anthocyanins have a range of biological activities that may produce health benefits; examples ranging from inhibition of DNA damage in cancer cells in vitro (Hou, 2003), protection against oxidative stress (Igarashi 2000), inhibition of digestive enzymes (McDougall and Stewart, 2006), induction of insulin production in isolated pancreatic cells (Jayaprakasam et al., 2005), reduction in inflammatory responses (Tall et al., 2004) to protection against age-related decline in brain function (Lau et al., 2006). Additionally, eating anthocyanin-rich fruits, extracts or pure anthocyanins may prevent or suppress disease states in vivo (Ramirez-Tortosa et al., 2001 and Mazza et al., 2002). Beside the anthocyanins, which are exclusively present in red cabbage, red cabbage has a higher Vitamin C and phenolic content compared to white or savoy cabbage, all of which protect against oxidative damage (Jagdish et. al., 2006, Scientia horticulturae 2006; 108:233-7). Furthermore it has been reported that red cabbage ameliorates diabetic effects in mammals (Hazem A. H. Kataya et al., 2007 eCAM Apr. 27, 2007). However, beside the described positive effects, presence of large amounts of anthocyanins cause problems, which make red cabbage difficult to handle. Anthocyanins are widely used as colouring agents and are proven food colours within the European Union (i.e. E-163). The anthocyanins stain skin, clothes, paper, textiles and stoneware, which make it difficult to handle for the producer and the consumer. The water soluble red pigment leaking out of fresh cut leaves leads to a discolouration of the plant material. To avoid the leakage, the red cabbage leaves are slightly dried out, which gives a poorer, less fresh appearance as for example white cabbage. Furthermore, the colour of the anthocyanins can turn dark-blue or dark-purple during the production of pickled cabbage resulting in an unappetizing appearance. Consequently, pickled cabbage is nearly exclusively produced from white cabbage. However, the absence of nameable amounts of anthocyanins in white or savoy cabbage has the disadvantage that said vegetables have a reduced health benefit and a less attractive appearance for the consumer. Furthermore, due to the absence of any colour, enzymatic browning, occurring at the edges of cut leaves, is highly visible leading to a less fresh appearance and, therefore, to economic losses.

It is therefore an objective of the present invention to provide new cabbage plants (e.g. *Brassica oleracea capitata* germplasm), which overcomes the above described drawbacks of the red and/or white cabbage varieties with respect to food application purposes. Hence, it was an objective of the invention to provide new *Brassica oleracea capitata* germplasm that is at least as suited for the production of Sauerkraut and even better suited for being used as salad/Sauerkraut as red cabbage. Additionally, it was an objective of the present invention to provide new *Brassica oleracea capitata* germplasm which is (i) less prone to enzymic browning and/or (ii) in which the enzymic browning is less visible due to anthocyanin pigmentation and (iii) which can be used directly in salad mixtures without having the necessity to partially dry out the leaves in order to prevent leakage of anthocyanins from the cut leave areas and (iv) which has reduced colouration/staining properties compared to red cabbage.

Surprisingly, it has been found that the anthocyanin content of plants produced by pollinating a red-cabbage with a white- or savoy-cabbage—or vice versa—does not correspond to an intermediate phenotype, although the leaf colour of said plants is pink. The skilled person would have expected an intermediate inheritance pattern and that the anthocyanins present in the leaves of the F1 plants would account for half the amount of anthocyanins present in red cabbage. This assumption is furthermore supported by the pink colour of the leaves of said hybrid plants. However, it has been found that the amount of anthocyanins present in the leaves of the F1 plants only constitute around one fourth of the anthocyanins present in red cabbage leaves. This unexpected inheritance pattern has lead to the provision of hybrid pants combining the advantages of their parent plants without showing their disadvantages. Said plants are suited for Sauerkraut production and producing health beneficial anthocyanins, without having the unwanted staining properties of red cabbage or the susceptibility for enzymatic browning of white cabbage.

Consequently, the above mentioned objectives have been achieved surprisingly by the subject matter as described in the appended claims.

SUMMARY OF THE INVENTION

The invention relates to a method for the production of a *Brassica oleracea* var. *capitata* (cabbage) hybrid plant comprising the steps:
a) pollinating a red-cabbage plant with a white- or savoy-cabbage plant, wherein the red cabbage plant can be used as male or female and wherein the female plant is male sterile;
b) harvesting the F1 seeds resulting from the pollination step performed under a)
c) sowing the F1 seeds obtained under b) and cultivating the resulting plants to produce mature plants; and optionally
d) harvesting the cabbage.

In a preferred embodiment of the invention, the intercostal areas of the leaves of the hybrid plant produced according to the above described method have a colour ranging from 79C to N83D, preferably from 79C to 82C measured with reference to the colour patch of The Royal Horticulture Society Colour Chart.

Particularly preferred is the above described method, wherein the hybrid plant has been produced by pollinating a *Brassica oleracea* var. *capitata* (L) Alef var. *rubra* DC plant with a *Brassica oleracea* var. *capitata* (L) Alef. var. *alba* DC or a *Brassica oleracea* var. *capitata* (L) Alef. var. *sabauda* DC plant.

The invention refers furthermore to a method for the production of a *Brassica oleracea* var. *capitata* (cabbage) hybrid plant as mentioned above, wherein the leave extracts of the resulting hybrid plants have an absorption measured at 524 nm using a spectrophotometer (leave extract absorption) of (i) at least more than 500% of the white- or savoy-cabbage parent plant; and (ii) not more than 40% of the red cabbage parent plant, wherein, the leave extracts used for the measurement are produced by extracting identical leave samples in 4% phosphoric acid.

In an additionally preferred embodiment of the invention, the red cabbage plant used as male or female is male sterile or self incompatible.

An additional embodiment of the invention relates to a method for the production of *Brassica oleracea* var. *capitata* seeds comprising the steps:

e) pollinating a red-cabbage plant with a white- or savoy-cabbage plant, wherein the red cabbage plant can be used as male or female and wherein the female plant is male sterile or the plants are self incompatible, f) harvesting the F1 seeds resulting from the pollination step performed under e).

The invention furthermore relates to a pink *Brassica oleracea* var. *capitata* plant containing a DNA sequence conferring male sterility or being able to confer male sterility or which is self incompatible. A preferred embodiment of the invention relates to a pink *Brassica oleracea* var. *capitata* plant, wherein the plant is male sterile and the male sterility is based on cytoplasmic male sterility (CMS) or nuclear male sterility (NMS). An even more preferred embodiment of the invention relates to a male sterile pink *Brassica oleracea* var. *capitata* (cabbage) plant, wherein the intercostal areas of the leaves of said cabbage have a colour ranging from 79C to N83D, preferably from 79C to 82C measured with reference to the colour patch of The Royal Horticulture Society Colour Chart. Especially preferred is a pink *Brassica oleracea* var. *capitata* (cabbage) plant as describe above, wherein the hybrid plant is produced by pollinating a red-cabbage plant with a white- or savoy-cabbage plant, wherein the female plant is male sterile. Particularly preferred parent plants are the red cabbage *Brassica oleracea* var. *capitata* (L) Alef. var. *rubra* DC, the white cabbage *Brassica oleracea* var. *capitata* (L) Alef. var. *alba* DC and the savoy cabbage *Brassica oleracea* var. *capitata* (L) Alef. var. *sabauda* DC plant. Particularly preferred are pink cabbage hybrid plants wherein the leave extracts of the resulting hybrid plants having an absorption measured at 524 nm using a spectrophotometer of 1) at least more than 500% of the white- or savoy-cabbage parent plant; and 2) not more than 40% of the red cabbage parent plant, wherein, the leave extracts used for the measurement are produced by extracting identical leave samples in 4% phosphoric acid.

Additionally, the invention relates to a method for the production of pink pickled cabbage by a fermentation process, comprising the steps of:

g) providing heads of a pink *Brassica oleracea* var. *capitata* plant or a plant produced according to the above described method, h) shredding of the heads, i) adding salt to the shredded plant material to a final concentration ranging from 2 to 3% of cabbage weight, j) incubating the shredded material under conditions suitable for the fermentation process and for a time period sufficient to complete the fermentation process.

In a yet another preferred embodiment, the pink pickled cabbage of the invention is produced using a progeny plant of the above described pink *Brassica oleracea* var. *capitata* F1 hybrid plant.

The invention relates furthermore to pickled cabbage, wherein the colour of the pickled cabbage after the above described fermentation process has a colour ranging from from 186A to 186C or 58A to 59C measured with reference to the colour patch of The Royal Horticulture Society Colour Chart. In a preferred embodiment, the invention relates to the above described pink *Brassica oleracea* var. *capitata* hybrid plant or the pink pickled cabbage, wherein the cell sap, released after cutting or shredding the leaves of the hybrid plants, stains surfaces much less than cell sap released from red cabbage.

In another embodiment, the invention relates to the use of a pink cabbage plant described above, with leaves having a colour ranging from 79C to N83D, preferably from 79C to 82C measured with reference to the colour patch of The Royal Horticulture Society Colour Chart for the production of pink pickled cabbage or pink cabbage salad, wherein the salad can be a mixture of different vegetables.

GENERAL DEFINITIONS

It is to be understood that this invention is not limited to the particular methodology, protocols, plant species or genera described as such. It must be noted that as used herein and in the appended claims, the singular forms "a" and "the" include plural reference unless the context clearly indicates otherwise. Thus, for example, reference to "a hybrid plant" is a reference to one or more plants and includes equivalents thereof known to those skilled in the art.

"About": is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). As used herein, the word "or" means any one member of a particular list.

"A DNA sequence conferring male sterility" or "a DNA sequence able to confer male sterility": in the context of a hybrid plant containing said DNA sequence, it refers to a hybrid plant that has been produced by using a male sterile female parent plant and, therefore, carries a DNA sequence conferring male sterility without necessarily being male sterile (e.g. in case that a restorer line has been used as the male parent plant). When restorer lines will be used, the plant cells of the resulting offspring comprising a DNA sequence which is able to confer male sterility, without being male sterile.

"Conditions suitable for the fermentation process and for a time period sufficient to complete the fermentation process" refers to the lacto-fermentation based pickled cabbage production process. The conditions for the production of pickled cabbage are well known to the skilled person and are described in the literature since the beginning of the 20$^{th}$ century (e.g. production of pickled cabbage has been described by Creuss, "Commercial Fruit and Vegetable Products", McGraw-Hill Book Co., 1958, p. 722-725, Frazer in "Food Microbiology", McGraw-Hill Book Co., 1967, p. 199-212; Pederson, C. S. 1930. Floral changes in the fermentation of sauerkraut. N.Y. Agr. Exp. St. Geneva Bull. 168; Pederson, C. S. 1960. Sauerkraut, p. 247. In C. O. Chichester, E. M. Mrak, and G. F. Stewart (ed), Advances in food research, vol. 10 Academic press, Inc., New York; Steinbruch, E., and O. L. Staden. 1964. Sauerkraut: processing of sauerkraut, p. 41, Annual reports of the Sprenger Inst., Wageningen, The Netherlands).

"Fermentation process": in the context of the present invention refers to the lacto fermentation process used for the production of pickled cabbage as described above.

"Hybrid plant" refers to plants produced by pollinating the pistil of one plant with the pollen of another, whereby the plants belong to different populations, breeds or cultivars within a single species (e.g. crosses between a *Brassica oleracea* var. *capitata* (L) Alef var. *rubra* DC plant with a *Brassica oleracea* var. *capitata* (L) Alef var. *alba* DC plant). In plant breeding, hybrids are commonly produced and selected because they have desirable characteristics not found or inconsistently present in the parent individuals or populations. Preferably, the parent plants are two different parent cultivars, each of which are inbred for a number of generations to the extent that they are almost homozygous, ensuring a phenotypically uniform F1 generation (filial).

"Male sterile": refers to plants unable to produce functional anthers, pollen, or male gametes. Male sterile plants are widely used to ensure large scale production of pure F1 hybrid seeds. According to the inventive method, the male sterility can be based on genetic or non-genetic factors. In case of the non-genetic type, the male sterility might be based on chemical substances or environmental or physiological parameters. Based on the location of genes controlling the male sterility such systems can be classified as (i) nuclear male sterility (nms or gms for genic male sterility) and (ii) cytoplasmic-nuclear male sterility (cnms or cms). The nms or cnms can occur spontaneously or can be artificially induced through mutagenesis (Induction of mutations for cytoplasmic male sterility and some rare phenotypes in Indian mustard (*Brassica juncea* L.). Indian Journal of Genetics & Plant Breeding. 61(4). November, 2001. 335-340; Male sterile broccoli (*Brassica oleracea* var. *italica*) induced by in vitro mutagenesis. Cruciferae Newsletter. 1987. 12, 50-51), protoplast fusion (e.g. as described in U.S. Pat. No. 5,917,128, examples 1 to 9, columns 4 to 12) or genetic engineering. The skilled person is aware of the existence of cabbage plants showing nms or cmns based male sterility (Ogura. 1968, Pearson. 1972, Nieuwhof. 1961, Fang et al., 1997, Wang et al., 1998, Pelletier et al., 1995). Nms is controlled by genes from the nuclear compartment. It is possible that Nms based male sterility is combined with environmental parameters (like temperature) in so called conditional mutants or e-nms lines (e.g. thermo sensitive- or photoperiod sensitive-genic male sterility in cabbage; Rundfeldt, H., 1961, Z. Pflanzenzucht 44: 30-62). Examples of male sterile plants and method for the production thereof are well known in the art (Analysis of genic male sterility in *Brassica oleracea*. Journal Euphytica, Publisher Springer Netherlands, Issue Volume 68, Numbers 1-2/January, 1993, Pages 53-57; A male sterile line with dominant gene (Ms) in cabbage (*Brassica oleracea* var. *captata*) and its utilization for hybrid seed production. Journal Euphytica, Publisher Springer Netherlands, Issue Volume 97, Number 3/November, 1997, Pages 265-268; Production of new CMS *Brassica oleracea* by transfer of 'Anand' cytoplasm from *B. rapa* through protoplast fusion, Journal of Theoretical and Applied Genetics, Issue Volume 94, Number 2/February, 1997, Pages 204-212; U.S. Pat. No. 5,254,802).

The cnms is the result of incompatibility between a recessive nuclear gene (maintainer gene) and the male sterile specific cytoplasmic genome (e.g. mitochondria genome). Nuclear genes capable of reversing the cnms are called restorer genes. If the fruits of the F1 hybrids are important, it is necessary that the male parent line carries the restorer gene. This is not necessary where vegetative parts of the plant are of economic value (e.g. cabbage). Male sterile female plants that can be used as parent plants in the method of this invention can be created by several cycles of backcrossings with fertile parent plants.

The skilled person is aware of methods for producing CMS lines. The initial step of one method to produce CMS lines is the transfer of the Ogura CMS germplasm from radish to *Brassica oleracea* by protoplast fusion. The CMS is than introgressed by back crossing into preferred elite lines. In a preferred embodiment of the invention, the CMS lines used as parent lines (deposited under NCIMB 41492 *Brassica oleracea* var *capitata* (L) Alef var *rubra* and NCIMB 41493 *Brassica oleracea* var *capitata* (L) Alef var *alba*; date of deposit: 31 Aug. 2007; NCIMB Ltd Ferguson Building, Craibstone Estate Bucksburn, Aberdeen) have been backcrossed 8 times with an elite parent line.

"Open pollination" refers to pollination by insects, birds, wind, or other natural mechanisms.

"Pink" when used in connection with *Brassica oleracea* plants refer to a colour of the intercostals areas of mature leaves of said plants ranging from 79C to N83D, preferably from 79C to 82C measured with reference to the colour patch of The Royal Horticulture Society Colour Chart (RHSCC). The RHSCC is the standard reference for plant colour identification and can be purchased from The Royal Horticulture Society (http://www.rhs.org.uk/publications/pubs_library_colourchart.asp). To determine the leave colour of a hybrid plant produced according to the invention, the colour of the intercostal areas of the mature leaves of said plants is compared with the RHSCC. Preferably, the term pink, when used in connection with "pink *Brassica oleracea* hybrid plants", refers to the colour of the internal mature leaves of said plants, which, on both sides, having a colour ranging from 79C to N83D, preferably from 79C to 82C measured with reference to the colour patch of The Royal Horticulture Society Colour Chart. The veins the mature leaves of the "pink *Brassica oleracea* hybrid plant" can have a white colour. The external leaves of the pink *Brassica oleracea* hybrid plants" can show greenish leaves with some anthocyanin pigmentation.

"Pink pickled cabbage": refers to pickled cabbage produced from the pink cabbage plants of the invention. Pink pickled cabbage does not refer to pickled cabbage turned red/pink as a result of the fermentation process. This discolouration has been observed occasionally as the result of an improper fermentation process. The red/pink discolouration of pickled cabbage is due the presence of yeasts or *Lactobacillus brevis* and is pH dependent and occurs during the post logarithmic phase of growth (Stamer et al., Induction of red colour formation in cabbage juice by *L. brevis* and its relationship to pink sauerkraut. 1973, Applied Microbiology, p. 161-166; Peterson C. S and Kelly C. D. 1938 Development of pink colour in sauerkraut. Food. Res. 3: 583-588).

"Red-cabbage plant" and/or "white- or savoy-cabbage plant" refers to plant varieties of the genus *Brassica oleracea* var. *capitata* differing in their leave colour, as a result of different amounts of anthocyanins present in their leaves.

Examples of said plants can be found at the ECPGR *Brassica* database (http://documents.plant.wur.nl/cgn/pgr/brasedb/). Red-cabbage plants are cultivars of the plant species *Brassica oleracea capitata rubra*. Said plants can be found within the mentioned database by using the following search profile:
Genus: *Brassica*
Species: *oleracea*
Subtaxon: *capitata rubra*

When using the above indicated search profile, 262 red cabbage plants can be identified, which are individualised by specific accession numbers, accession names and the source of said germplasm. White-cabbage plants are cultivars of the plant species *Brassica oleracea capitata alba* or *sabauda*. Said plants can be found within the ECPGR *Brassica* database by using the following search profile:
Genus: *Brassica*
Species: *oleracea*
Subtaxon: *capitata alba*, or *sabauda*

When using the above indicated search profile, 1476 white cabbage varieties and 429 *sabauda* varieties can be identified. Furthermore, the skilled person is aware of the nature of the mentioned cabbage plants and knows how to obtain said plant varieties.

"Sauerkraut", "pickled cabbage", "sour cabbage" or "acidic cabbage": are used inter-changeable and refer to the result of a natural fermentation caused by bacteria indigenous to cabbage in the presence of 2 to 3% salt. The salt can be replaced by a mixture of ethanol and an ingestible acid selected from the group of acetic acid, lactic acid, malic acid, citric acid, phosphoric acid, and mixtures thereof as described in U.S. Pat. No. 5,064,662. The fermentation yields lactic acid as the major product. The production of pickled cabbage is state of the art and known to the skilled person. In the production of pickled cabbage, the heads of mature cabbage are washed and shredded and salt is added to the cabbage to a final concentration ranging between 2 and 3%, preferably 2.5%. The salted cabbage is protected from oxygen by tightly packing into useful containers known to the skilled person. The fermentation process takes about five weeks and it is important to assure that gases produced during the fermentation can escape from the container. A temperature of about 20° C. is preferred for the fermentation process. The salting of the cabbage serves two major purposes. First, it causes an osmotic imbalance which results in the release of water and nutrients from the cabbage leaves. The sap of the shredded cabbage cells, which is released due to the osmotic pressure resulting from the high salt environment, is an excellent growth medium for the microorganisms needed for the fermentation process. The salt must be even distributed to avoid areas of high and low salt concentrations. The exclusion of oxygen is critical for the fermentation process to assure that only the desired microorganisms are able to grow and that the growth of spoilage organisms is prevented. The fermentation process can start with microorganisms present in the cabbage leaves. As soon as the pH drops, the environment becomes favourable for the heterofermentative strains of leuconostoc, which produce much carbon dioxide and acid, leading to a continuous drop in the pH of the system. Later in the process, *lactobacillus* stains displace the leuconostoc strains.

"Self-incompatibility" refers to the genetic mechanisms in plants, which prevent self-fertilization. When a pollen grain produced by a Self-incompatible plant reaches a stigma of the same plant, the process of pollen germination, pollen tube growth, ovule fertilization, and/or embryo development is halted, and consequently no seeds are produced. In *Brassica oleracea* this self-recognition mechanism is found (Olsson, G., 1960: Self-incompatibility and outcrossing in rape and white mustard. Hereditas 46, 241-252).

DETAILED DESCRIPTION OF THE INVENTION

The teaching of the present invention enables the production of new *Brassica oleracea* var. *capitata* (cabbage) germplasm useful for the production of vegetable based food-stuff by overcoming some drawbacks related to the use of white- and/or red-cabbage varieties related to the production of pickled cabbage or the use as fresh salad.

A first embodiment of the invention relates to a method of producing a *Brassica oleracea* var. *capitata* (cabbage) hybrid plant comprising the steps:
a) pollinating a red-cabbage plant with a white- or savoy-cabbage plant, wherein the red cabbage plant can be used as male or female and wherein the female plant is male sterile,
b) harvesting the F1 seeds resulting from the pollination step performed under a)
c) sowing the F1 seeds obtained under b) and cultivating the resulting plants to produce mature plants, and optionally
d) harvesting the cabbage.

An additional embodiment of the invention relates to the production of *Brassica oleracea* var. *capitata* (cabbage) seeds comprising the following steps:
e) pollinating a red-cabbage plant with a white- or savoy-cabbage plant, wherein the red cabbage plant can be used as male or female and wherein the female plant is male sterile,
f) harvesting the F1 seeds resulting from the pollination step performed under step e).

The harvested seeds can be used for the production of cabbage plants as described above. An additional embodiment of the invention are the seeds produced in accordance with the above described inventive method.

The pollinating steps a) and e) described above refer to sexual crossing or cross-fertilisation between two parent plants or plant populations, one performing the role of the male, the other of the female. The plant used as a female plant is male sterile, i.e. the cytoplasm of the cells of said plant contains organelles possessing nucleotide sequences conferring male sterility, and, preferably, good agronomic characteristics. The male sterility system enable female plants to be obtained which are incapable of self-fertilisation, and from which, after pollination, the seeds, which are all uniform hybrids, can be harvested directly. Laborious techniques, such as castration of the flowers, are not necessary. The genetic characteristic of male sterility is transferred exclusively by the mother plant, and 100% of male sterile offspring is produced. Male sterile Crucifereae plants are known in the art since a long time. The first male sterile Cruciferae plant has been described by Ogura in 1968 (*Raphanus sativus*). Examples of male sterile systems in Brassicacae plants and methods how to produce them are described in the art and known to the skilled person. Bannerot et al. produced male sterile *Brasscica oleracea* plants by transferring the "Ogura cytoplasm" to *Brasscica oleracea* (Bannerot, H., L. Boulidard, Y. Cauderon & J. Tempe, 1974. Transfer of cytoplasmic male sterility from *Raphanus sativus* to *Brassica oleracea*. Proc. Eucarpia Meeting-Cruciferae (1974): 52-54). U.S. Pat. No. 5,254,802 discloses *Brasscica oleracea* plants that contain the "Ogura cytoplasmic male sterility (CMS) cytoplasm", which have been produced using the protoplast fusion technique. U.S. Pat. No. 6,046,383 describes *Brasscica oleracea* plants which contain the Polima CMS cytoplasm (see also e.g. U.S. Pat. Nos. 5,789,566, 5,917,128 or EP 0810 284 B1). The production of the above described hybrids can be done by e.g. using a fixed red or white cabbage variety, developed by classical inbreeding methods like self pollination, mass pollination or by dihaploidisation, as the male parent plant. Since the vegetative parts of the cabbage plants are of commercial interest, it is not necessary to use male parent plants able to restore the male-fertility of the produced offspring. This is different if the interest lies in the seeds produced by the hybrid offspring plants (F2 seeds). In this case the male-fertility needs to be restored. Restoration of pollen fertility is achieved by means of pollinator parent lines carrying nuclear dominant restorer genes. Hence, for the above described inventive method, the used male parent plant can be—but does not need to be—a restorer line.

In a preferred embodiment, the invention relates to the production of pink *Brassica oleracea* var. *capitata* (cabbage) hybrid plants as describe above, wherein the intercostal areas of the leaves of the produced cabbage have a colour ranging from 79C to N83D, preferably from 79C to 82C as measured with reference to the colour patch of The Royal Horticulture Society Colour Chart The Royal Horticultural Society (RHS) has been publishing the RHS Colour Chart since 1966. It has been widely used for the phenotypically characterisation of plant varieties, and is a known standard reference for plant colour identification well known to the skilled artisan. In an additionally preferred embodiment, the leave extracts of the *Brassica oleracea* var. *capitata* (cabbage) hybrid plants produced according to the method of the invention having an absorption measured at 524 nm using a spectrophotometer of 1) at least more than 500%, preferably at least more than 600% or more than 700%, more preferably at least more than 800% or more than 900%, particularly preferably at least more than 1000% of the white- or savoy-cabbage parent plant; and 2) not more than 40%, preferably not more than 35%, more preferably not more than 30, particularly preferably not more than 29%, 28%, 27%, 26%, 25% or 20% of the red cabbage parent plant, wherein, the leave extracts used for the measurement are produced by extracting identical leave samples in 4% phosphoric acid (see Example 2). The skilled person is aware of method for the determination of anthocyanins in cabbage leaves. The anthocyanin content of cabbage leaves can be determined using a spectrophotometer (e.g. Spectrophotometer Ultrospec III (Phamacia LKB) or Perkin Elmer Model 510), reading the extract absorbance at 530 nm. Considering that cabbage anthocyanins all derive from cyanidin glucoside, quantitative data can be expressed as cyanidin-3-glucoside, whose molar extinction in 1% HCl in methanol is 34.300. (Methods of analysis for anthocyanins in plants and biological fluids. By G. Mazza, Juan E. Cacace and Colin D. Kay. J AOAC Int. 2004 January-February; 87(1):129-45). Francis F J, Analysis of anthocyanins, in Anthocyanins as Food Colors, Ed by Markakis P, Academic Press, New York, pp 181-207 (1982)).

In a furthermore preferred embodiment of the invention, the hybrid plant or the seeds produced according to the above described inventive methods have been produced by pollinating a *Brassica oleracea capitata rubra* plant with a *Brassica oleracea capitata alba* or a *Brassica oleracea capitata sabauda* plant, wherein the female plant is male sterile. Varieties that are particularly preferred are *Brassica oleracea* var. *capitata* (L) Alef. var. *rubra* DC, *Brassica oleracea* var. *capitata* (L) Alef. var. *alba* DC or *Brassica oleracea* var. *capitata* (L) Alef. var. *sabauda* DCt. Additionally preferred plants are those male sterile plants listed in the ECPGR *Brassica* database (see definitions: "red-cabbage plant" and/or "white- or savoy-cabbage plant"). Particularly preferred are the male sterile white cabbage line WK989 deposited under NCIMB 41493 *Brassica oleracea* var *capitata* (L) Alef var *alba* and the red cabbage fertile line RK015, deposited under NCIMB 41492 *Brassica oleracea* var *capitata* (L) Alef var *rubra* on 31 Aug. 2007. On embodiment of the present invention relates to pink cabbage plants having the leave colour of the pink cabbage resulting from the pollination of the male sterile white cabbage line WK989 deposited under NCIMB 41493 with pollen derived from the red cabbage fertile line RK015, deposited under NCIMB 41492. Beside the use of male sterile plants, another embodiment of the present invention is the use of at least one self incompatible parent inbreed line for the production of the inventive hybrid plants.

Additionally, the invention relates to a pink *Brassica oleracea* var. *capitata* (cabbage) plant containing a DNA sequence conferring male sterility. In a preferred embodiment, the plant is male sterile and the male sterility is based on cytoplasmic male sterility (CMS) or nuclear male sterility (NMS).

The pink *Brassica oleracea* var. *capitata* (cabbage) plant of the invention has pink coloured intercostal leaf areas, wherein the colour ranges from 79C to N83D, preferably from 79C to 82C as measured with reference to the colour patch of The Royal Horticulture Society Colour Chart. In an especially preferred embodiment, the pink *Brassica oleracea* var. *capitata* (cabbage) plant of the invention is a hybrid plant produced as described above. Particularly preferred is a pink *Brassica oleracea* var. *capitata* (cabbage) hybrid plant produced by pollinating a *Brassica oleracea* var. *capitata* (L) Alef. var. *rubra* DC plant with a *Brassica oleracea* var. *capitata* (L) Alef. var. *alba* DC or a *Brassica oleracea* var. *capitata* (L) Alef. var. *sabauda* DC plant. Particularly preferred is a pink *Brassica oleracea* var. *capitata* plant produced by pollinating the male sterile white cabbage line WK989 (deposited under NCIMB 41493) and the red cabbage fertile line RK015 (deposited under NCIMB 41492). An additional embodiment of the invention are pink *Brassica oleracea* var. *capitata* plants produced by crossing two pink cabbage plants, preferably crossing of plants that have been produced as described above. In this respect it has to mention that the inheritance pattern of the offspring produced by using the pink cabbage as parent plant(s) will follow the "law of independent assortment", also known as Mendel's Second Law.

An additional subject matter of the pertinent invention relates to a method for the production of pink pickled cabbage by a fermentation process, comprising the steps of:
a) providing heads of a pink *Brassica oleracea* var. *capitata* plant,
b) shredding the heads,
c) adding salt to the shredded plant material to a final concentration ranging from 2 to 3% of cabbage fresh weight,
d) incubating the shredded material under conditions suitable for the fermentation process and for a time period sufficient to complete the fermentation process.

As described in U.S. Pat. No. 5,064,662, the salt can be replaced by a mixture of ethanol and an ingestible acid selected from the group of acetic acid, lactic acid, malic acid, citric acid, phosphoric acid, and mixtures thereof.

The pink *Brassica oleracea* var. *capitata* hybrid plant according to step g) described above can be produced by pollinating a red-cabbage plant with a white- or savoy-cabbage plant according to the inventive method defined above. Beside that, each plant listed as *Brassica oleracea capitata rubra* and *Brassica oleracea capitata alba* or *sabauda* in the ECPGR *Brassica* database (http://documents.plant.wur.nl/cgn/pgr/brasedb/) can in principle be used as parent plant. The person skilled in the art is aware of additional sources of useful germplasm. Furthermore, male-fertile, self incompatible and/or male-sterile parent plants can be used for the provision of a pink *Brassica oleracea* var. *capitata* plant used in step g) above. Hence, the pink hybrid plant can also be produced by open pollination. The parent lines can be produced by inbreeding methods known to the skilled person.

In a particularly preferred embodiment of the invention, the pink *Brassica oleracea* var *capitata* hybrid plant according to step g) has been produced according to the above described inventive method and contains a DNA sequence conferring male sterility. In an most preferred embodiment, said plant is a male sterile plant. Additionally, the pink *Brassica oleracea* var. *capitata* plant can be an offspring of the hybrid plants produced as described above. In this case it is necessary to use a male restorer line for the production of the F1 hybrid plants as described above.

The conditions for the production of pickled cabbage are well known to the skilled person and described in the literature (see above and example 3). Red cabbage leaves turn into purple or blue colour during the above described Sauerkraut preparation process. This does not happen when the pink *Brassica oleracea* var. *capitata* plants of the present invention are used, which change their colour during the fermentation process from 79C to N83D to from 186A to 186C or 58A to 59C measured with reference to the colour patch of The Royal Horticulture Society Colour Chart.

An additional subject matter of the present invention relates to pink pickled cabbage. After the fermentation process the pickled cabbage has still a colour ranging from 186A to 186C or 58A to 59C measured with reference to the colour patch of The Royal Horticulture Society Colour Chart and said colour is not caused by a microorganism based discolouration (see Stamer et al., Induction of red colour formation in cabbage juice by *L. brevis* and its relationship to pink sauerkraut. 1973, Applied Microbiology, p. 161-166; and Peterson C. S and Kelly C. D. 1938. Development of pink colour in Sauerkraut. Food. Res. 3: 583-588.)

Figure 1:
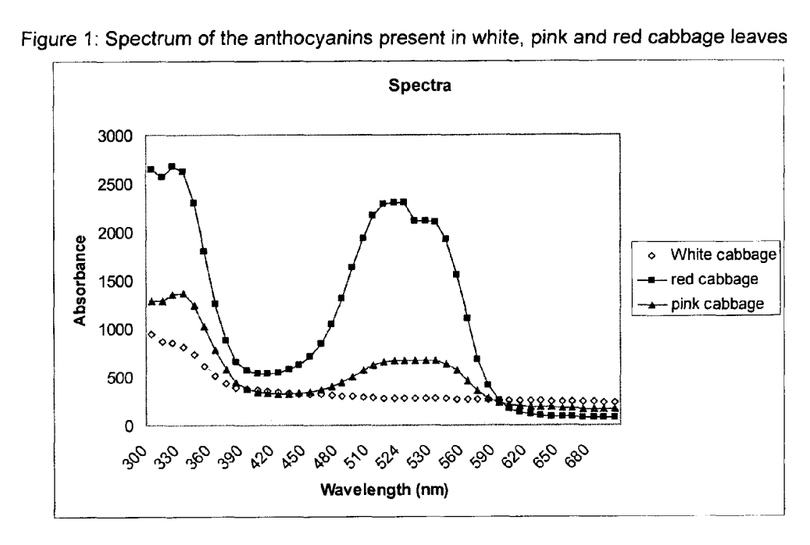
FIG. 1: Measurement of the anthocyanin content of white, red and pink cabbage at 524 nm using a Spectrophotometer.

The cell sap, released after mechanical destruction (e.g. cutting or shredding) from leaves of the above described pink *Brassica oleracea* var. *capitata* plants, or plants produced according to the inventive method, stains surfaces which absorb liquid colours (e.g. paper or clothes) to a much lesser extend compared to the cell sap released from red cabbage (see Example 2, FIG. 1). Hence, a preferred embodiment of the invention relates to pink *Brassica oleracea* var. *capitata* plants, wherein the cell sap, released after mechanical destruction (e.g. cutting or shredding) from leaves of said plants, stains surfaces which absorb liquid colours much less compared to the cell sap released from red cabbage. In this context, "much less staining" means a reduction of the staining capacity of the pink cabbage cell sap compared to the red cabbage cell sap (e.g. as determined in example 2) of 50%, preferably of 60%, more preferably of 70%, much more preferably of 75%, most preferably of 80%. Additionally, the leaves of the pink cabbage of the present invention, or cabbage produced according to the inventive method, show less discolouration of the edges of cut leaves. In this context, "less discolouration of the edges of cut leaves" refers to a reduction of the discolouration of the leave edges after cutting of 50%, preferably of 60%, more preferably of 70%, much more preferably of 75%, most preferably of 80%. This has the advantage that pink cabbage is much easier to handle and less care must be taken to avoid staining (by the producer as well as the consumer). Hence, pink *Brassica oleracea* var. *capitata* hybrid plants are particularly suited for (i) production of pickled cabbage (reduced staining properties) and (ii) pink cabbage salad, which must not be partially dried in order to prevent discolouration of the leave edges. Furthermore, presence of anthocyanins in the leaves of the pink cabbage plants lead to a reduced visibility of enzymatic browning effects, which again, lead to a fresher appearance of the salad.

Hence, an additional embodiment of the invention relates to the use of pink *Brassica oleracea* var. *capitata* plants as described above, or produced using the above described inventive method, for the production of pink pickled cabbage and pink cabbage salad, wherein the pink cabbage is preferably used in combination with other vegetables in a vegetable salad mixture. An additional embodiment is the above described pink cabbage salad or the vegetable salad mixture comprising pink cabbage as such.

EXAMPLES

The following examples are provided in order to demonstrate and further illustrate certain preferred embodiments and aspects of the present invention and are not to be construed as limiting the scope thereof.

Example 1

Plant Production a) Production of Pink Cabbage Plants
    a. Pollinating. Seeds of white cabbage and red cabbage have been sown between March and July. Plants of white and red cabbage are taken out of the field and transplanted together in a frost free greenhouse compartment. The plants started flowering in March/April. Bee hives have been added to the compartment and the flowering plants were pollinated by bees. The seed set was visible after 3 weeks of the first pollinations. The pollinated plants were kept in the greenhouse until the seed colour starts to change from green to brown black.
    b. Harvest of the seeds. The plants were cut by the stem and put on linen sleeves for several days to dry. The seeds were than trashed in a thrashing machine or the seeds were taken out by hand.
    c. Sowing the seeds. The seeds were sown in trays by hand or by machine. The trays are put in a frost free greenhouse and needs to grow, depending on the growing conditions between 6-10 weeks. The plants were than transplanted to the field.
    d. Harvest of the cabbage. The pink plants were harvested by hand with a knife. The knife is placed just under the cabbage head.

Example 2

Analysis of the Pink Cabbage Plants Obtained in Example 1

To analyse the differences between white, red and pink cabbage, 3 different methods have been used:
a) colour determination using the The Royal Horticulture Society Colour Chart;
b) leakage analysis and the reduction of leakage compared to red cabbage; and
c) non-staining characteristics of the pink-cabbage compared to red cabbage
Material and Instruments
    Analytical balance (Mettler AE260 Deltarange)
    Paper filters (folding filters 595 ½ diameter 150 mm, Schleicher & Schuell)
    Paper filters (Schleider & Schuell, whatman quality, circles with 110 mm diameter)

15 ml PP test tubes bio-one CellStar (Greiner) Cat no 188271

Spectrophotometer Ultrospec III (Phamacia LKB)

Cuvets half-micro 10×10×45 order nr 613101 (Greiner)

Colour chart (RHS colour chart, The royal horticultural society)

a) Colour Determination Using the the Royal Horticulture Society Colour Chart.

Colour Determination:

The colour of the intercostal areas of the mature cabbage leaves and of the veins have been determined using The Royal Horticulture Society Colour Chart (RHSC-Chart). The object was placed under the hole in the colour patch to identify the colour patch that matches the leave colour. For a general description of leaf colour take two or three examples representative of the cabbage head.

Result: The colour of the red and pink cabbage was in the ranges:

Pink Cabbage:

Colour range outside and inside: 79C/79D-N82C/83D

Colour range vein: 77A-N80A

Red cabbage: Colour range N186A-N187A b) Leakage Analysis

Leakage Measurement.

Weigh a round Whatman filter on an analytical balance. Cut the mature cabbage head into halves. Lay on one side of the cabbage a round Whatman filter (see materials above), don't press. Put a 5 kg weight on the filter.

Leave the filter for 60 sec on the cabbage. Put the filter immediately back on the analytical balance. The difference in weight is an indication of the leakage of the cabbage. The results are listed in table 1 and shown in FIG. 2. The leaking can be measured by the surface discoloured on absorption paper. Pink cabbage has less than 20% of the surface discoloured than red cabbage.

TABLE 1

Intercostal colour, leakage and absorbance of red, white and pink cabbage.

| | anthocyan | Average | Leaf colour using RHS Color-Charts | | |
|---|---|---|---|---|---|
| Nr. cabbages | average absorbance at 524 nm* | leaking (gr) | Vein | inside cabbage | outside cabbage |
| White (454) | 0.110 | 0.1538 | | | |
| Pink 1 (863) | 0.390 | 0.1892 | 77B | 79C | 79D |
| Pink 2 (879) | 0.297 | 0.1365 | 77B | 79C | 79D |
| Red 1 (409) | 3.061 | 0.1266 | 77A | 79A/79C | N186A |
| Red 2 (408) | 3.602 | 0.1497 | 77A | 79A/79C | N186B |

*10 times diluted

Anthocyanin Measurement

Cut a wedge out of the cabbage, the core of the cabbage has to stay out of the sample. Weigh 100 gram samples (in duplicate) and blend said samples in 4% phosphoric acid in a blender. The samples must be filtrated. Dilute the sample 10-times for red and pink cabbage. Pipette the sample in a micro-cuvet. Measure the absorbance by 524 nm (see results spectrum in Table 1 and absorbance in FIG. 1) using a spectrophotometer in accordance with instruction manual (e.g. Ultrospec III UV/visible Spectrophotometer). The absorbance in the filtrate is an indication of the amount of anthocyanin present in the cabbage leaves. From literature it is known that the optimal absorbance of anthocaynins present in plants is between 520-540 nm (Methods of analysis for anthocyanins in plants and biological fluids. By G. Mazza, Juan E. Cacace and Colin D. Kay. J AOAC Int. 2004 January-February; 87(1):129-45). Francis F J, Analysis of anthocyanins, in Anthocyanins as Food Colors, Ed by Markakis P, Academic Press, New York, pp 181-207 (1982)).

c) Non-Staining Characteristics of the Pink-Cabbage Compared to Red Cabbage.

Figure 2:
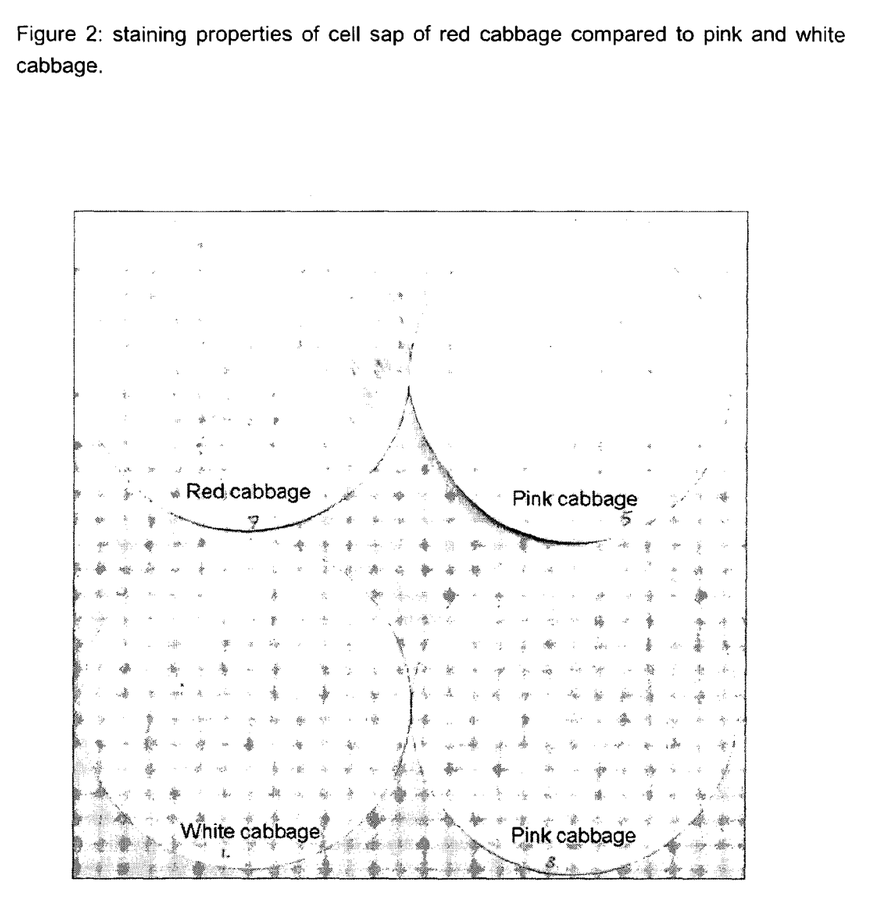
FIG. 2: Staining properties of cell sap of red cabbage compared to pink and white cabbage.

As illustrated in FIG. 2, the cell sap released from pink cabbage leaves stains filter paper much less compared to red cabbage. When cutting red cabbage the red coloured anthocyanins will paint human skin but also clothes, paper and other surfaces which absorb liquid colour. When cutting the pink cabbage there is no colour absorption on human skin, clothes, paper or other surfaces which absorb liquid colour.

Example 3

Production of Pickled Cabbage (Sauerkraut) Using the Plants Obtained in Example 1

In the production of Sauerkraut, mature cabbage heads are washed and shredded. The salt is mixed with the shredded cabbage to a final concentration of about 2.5%. The salted cabbage is then tightly packed into a tierce or crock. The cabbage is protected from air (oxygen) in a manner that will permit gases produced during the fermentation to escape. A temperature of about 20° C. is preferred for the fermentation. About five weeks is required for a complete fermentation.

The salting of the cabbage serves two major purposes. First, it causes an osmotic imbalance which results in the release of water and nutrients from the cabbage leaves. The fluid expelled is an excellent growth medium for the microorganisms involved in the fermentation. It is rich in sugar and growth factors. Second, the salt concentration used inhibits the growth of many spoilage organisms and pathogens. It does not, obviously, inhibit the desired floral succession. As cabbage is approximately 90% water and the salt is dissolved entirely in the water, the actual salt concentration (brine strength) experienced by the microorganisms in their aquatic milieu is around 2.8%. Thorough and even distribution of the salt is critical. Pockets of low or high salt concentration would result in spoilage and/or lack of the desired fermentation.

Preparation of Sauerkraut

Trim the cabbage heads, removing the outer leaves.

Wash the trimmed heads thoroughly with tap water.

Cut the heads in half, removing the hard, central core.

Shred the cabbage with the cabbage shredder.

Weigh the shredded cabbage. Mix in the salt such that a final concentration of 2.5% is achieved.

Pack the shredded cabbage into the crocks, filling to approximately 75-80% of total volume. Compress the mixture moderately while avoiding crushing or bruising the cabbage tissue.

Add the lid and weights and finally cover with cheesecloth.

Incubate the crocks at 21° C. for 8 weeks.

The resulting Sauerkraut had a colour ranging from 186A to 186C or 58A to 59C measured with reference to the colour patch of The Royal Horticulture Society Colour Chart

The invention claimed is:

1. Method for the production of a pink *Brassica oleracea* var. *capitata* (cabbage) hybrid plant for use as a food product comprising the steps:

a) pollinating a *Brassica oleracea* var. *capitata* (L) Alef. var. *rubra* DC plant with a *Brassica oleracea* var. *capitata* (L) Alef. var. *alba* DC plant, wherein the female plant is a plant of the male sterile white cabbage line WK989, seed of line WK989 having been deposited under NCIMB 41493, and the male parent is a plant of the red cabbage fertile line RK015, seed of line RK015 having been deposited under NCIMB 41492, b) harvesting F1 seeds resulting from the pollination step performed under step a), and c) sowing the F1 seeds obtained under b) and cultivating the resulting plants to produce mature plants, wherein the intercostal areas of the leaves of the produced cabbage have a colour ranging from 79C to N83D measured with reference to a colour patch of The Royal Horticulture Society Colour Chart.

2. The method according to claim 1 wherein the *Brassica oleracea* var. *capitata* hybrid plant has a leaf extract absorption value measured at 524 nm using a spectrophotometer of i) at least more than 500% of the *Brassica oleracea* var. *capitata* (L) Alef. var. *alba* DC parent plant; and ii) not more than 40% of the *Brassica oleracea* var. *capitata* (L) Alef. var. *rubra* DC parent plant, and wherein the leaf extracts used for the measurement are produced by extracting leaf samples in 4% phosphoric acid.

3. The method according to claim 1 wherein the intercostal areas of the leaves of the produced cabbage have a colour ranging from 79C to 82C measured with reference to a colour patch of The Royal Horticulture Society Colour Chart.

4. The method according to claim 1 wherein both sides of the internal mature leaves of the produced cabbage have a colour ranging from 79C to N83D measured with reference to a colour patch of The Royal Horticulture Society Colour Chart.

5. The method according to claim 1 wherein both sides of the internal mature leaves of the produced cabbage have a colour ranging from 79C to 82C measured with reference to a colour patch of The Royal Horticulture Society Colour Chart.

6. Method for the production of *Brassica oleracea* var. *capitata* (cabbage) seeds comprising the steps:

a) pollinating a *Brassica oleracea* var. *capitata* (L) Alef. var. *rubra* DC plant with a *Brassica oleracea* var. *capitata* (L) Alef. var. *alba* DC plant, wherein the female plant is a plant of the male sterile white cabbage line WK989, seed of line WK989 having been deposited under NCIMB 41493, and the male parent is a plant of the red cabbage fertile line RK015, seed of line RK015 having been deposited under NCIMB 41492, and b) harvesting F1 seeds resulting from the pollination step performed under step a), wherein the F1 seeds produce pink hybrid cabbage for use as a food product, and wherein the intercostal areas of the leaves of the produced cabbage have a colour ranging from 79C to N83D measured with reference to a colour patch of The Royal Horticulture Society Colour Chart.

* * * * *